(12) United States Patent
Lorenzo et al.

(10) Patent No.: US 6,749,633 B1
(45) Date of Patent: Jun. 15, 2004

(54) PRE-CRYSTALLINE INTRAOCULAR IMPLANT

(75) Inventors: Georges Lorenzo, Santa Fe (AR); Olivier Platon, Allauch (FR)

(73) Assignee: Ioltechnologie-Production, Perigny (FR)

( * ) Notice: Subject to any disclaimer, the term of this patent is extended or adjusted under 35 U.S.C. 154(b) by 81 days.

(21) Appl. No.: 10/129,817

(22) PCT Filed: Nov. 10, 2000

(86) PCT No.: PCT/FR00/03156
§ 371 (c)(1),
(2), (4) Date: Sep. 20, 2002

(87) PCT Pub. No.: WO01/34066
PCT Pub. Date: May 17, 2001

(51) Int. Cl.$^7$ .................................................. A61F 2/16
(52) U.S. Cl. ...................... 623/6.36; 623/6.28; 623/6.37
(58) Field of Search ................................ 623/6.11, 6.19, 623/6.29, 6.36, 6.37, 6.4, 6.43, 6.46, 6.47, 6.49, 6.24, 6.27, 6.28

(56) References Cited

U.S. PATENT DOCUMENTS

| | | | |
|---|---|---|---|
| 4,769,035 A | | 9/1988 | Kelman |
| 5,480,428 A | | 1/1996 | Fedorov et al. |
| 5,913,898 A | * | 6/1999 | Feingold ................... 623/6.36 |
| 6,015,435 A | * | 1/2000 | Valunin et al. ............ 623/6.28 |
| 6,106,553 A | * | 8/2000 | Feingold .................... 623/6.36 |
| 6,110,202 A | * | 8/2000 | Barraquer et al. ......... 623/6.43 |
| 6,428,574 B1 | * | 8/2002 | Valunin et al. ............ 623/6.28 |
| 6,457,826 B1 | * | 10/2002 | Lett ............................ 351/161 |
| 6,506,212 B2 | * | 1/2003 | Zhou et al. ................ 623/6.38 |
| 6,638,305 B2 | * | 10/2003 | Laguette .................... 623/6.37 |

FOREIGN PATENT DOCUMENTS

| | | | |
|---|---|---|---|
| DE | 42 11 265 C1 | 7/1993 | |
| EP | 0 592 813 A1 | 4/1994 | |
| FR | WO 01/08606 A1 | * 2/2001 | ................ 623/6.28 |
| GB | 2153688 A | 8/1985 | |
| WO | WO 98/30657 | 8/1997 | |
| WO | WO 98/17205 | 4/1998 | |

* cited by examiner

Primary Examiner—David H. Willse
Assistant Examiner—Suzette J. Jackson
(74) Attorney, Agent, or Firm—Young & Thompson

(57) ABSTRACT

A pre-crystalline intraocular implant adapted to be implanted between the front face of the crystalline lens and the iris. It comprises an optical part (31) and a haptic part. The haptic part comprises a haptic ring (32) surrounding the optical part (31), a peripheral band (34) and branches (33) linking the haptic ring (32) and the peripheral band (34). The rear face of the implant comprises a central portion with spherical surface having a first radius, a second annular spherical portion having a radius greater that the first radius and a third concentric portion with spherical surface having a radius greater than the second radius. The invention is useful for correcting ametropia of a phakic eye.

21 Claims, 2 Drawing Sheets

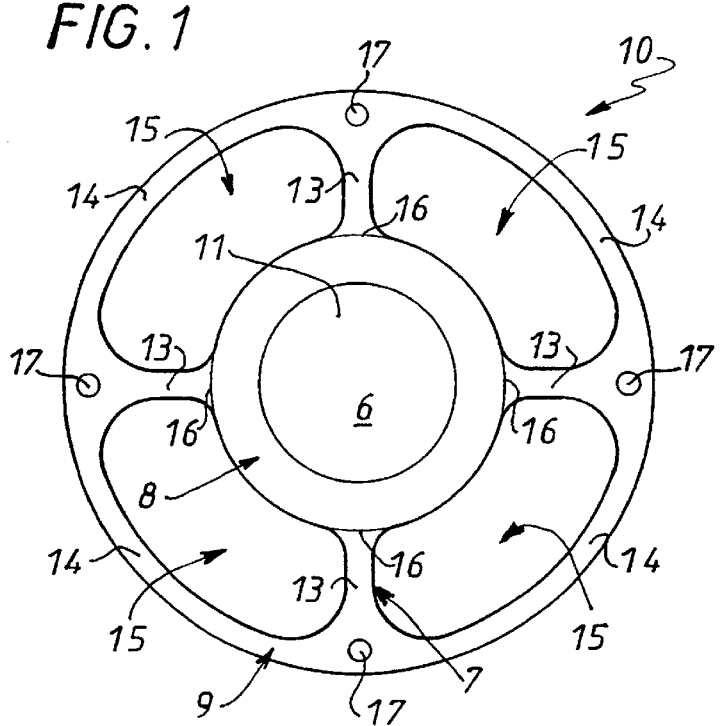
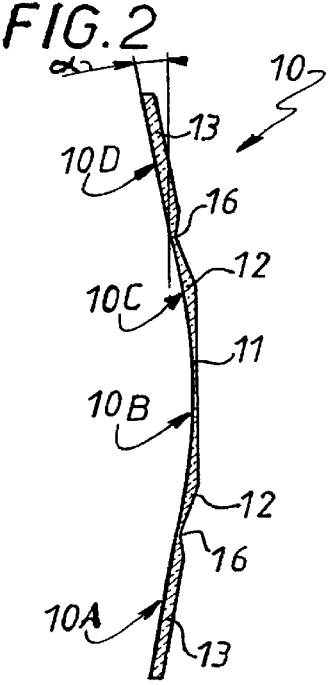
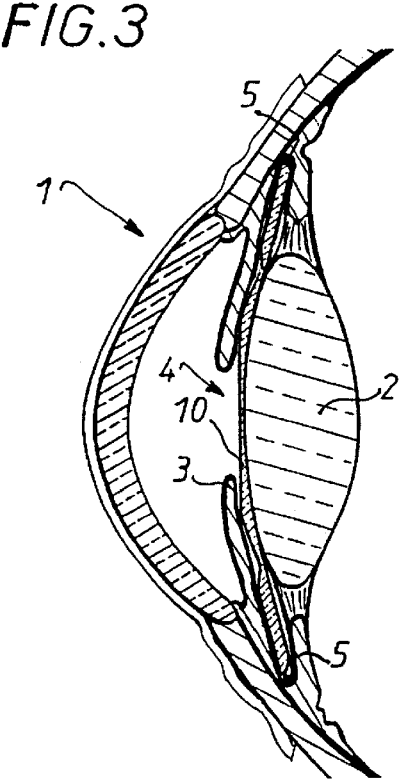
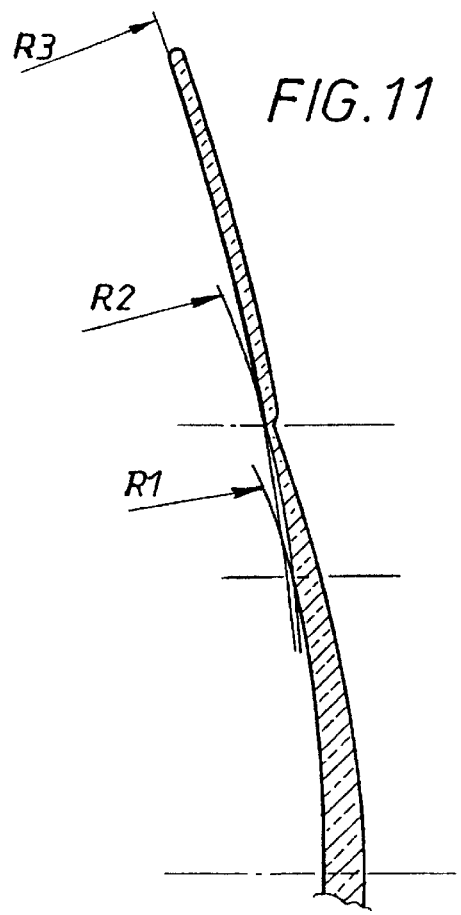

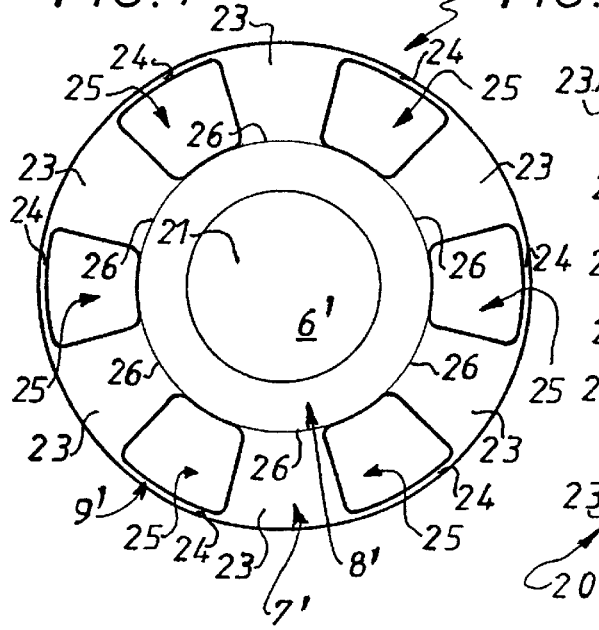
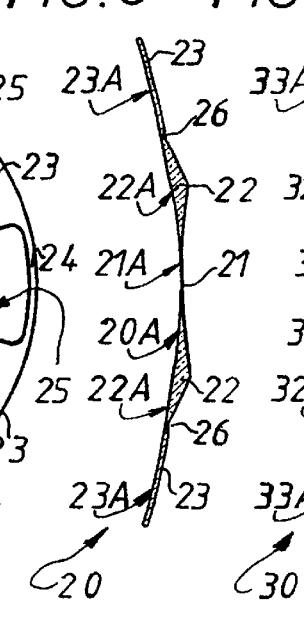
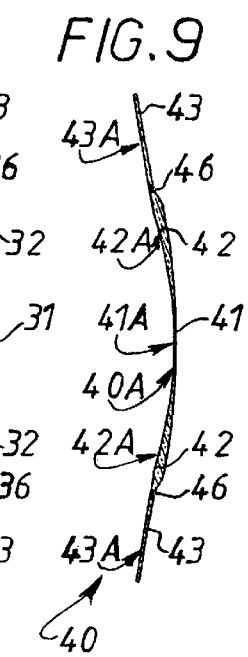
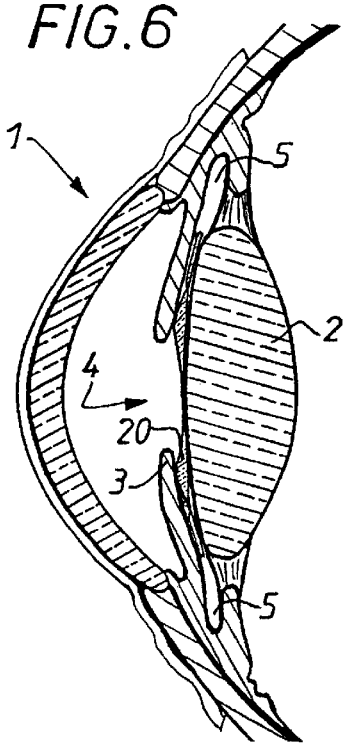
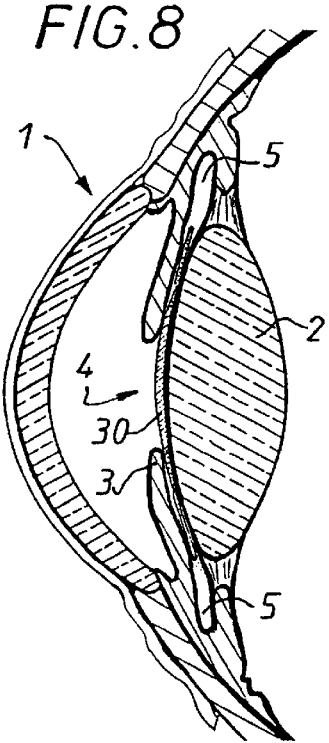
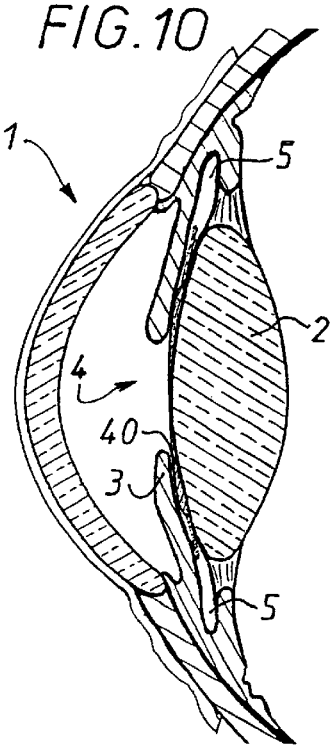

PRE-CRYSTALLINE INTRAOCULAR IMPLANT

The present invention relates to a precrystalline intraocular implant.

It relates generally to posterior chamber intraocular implants for a phakic eye, in particular for correcting ametropias of a young patient with a clear crystalline lens.

This kind of intraocular implant is implanted between the anterior face of the crystalline lens and the iris.

The narrowness and the environment of the space between the iris and the crystalline lens give rise to problems in the successful use of this type of implant. Too strong a contact with the posterior face of the iris can lead to depigmentation thereof and rubbing on the crystalloid can cause a cataract of the crystalline lens.

Similarly, this kind of implant is affected by anterior-posterior movements of the center of the crystalline lens during accommodation for near vision, which causes problems with stabilizing and centering this kind of implant.

The posterior surface of the optic of precrystalline implants is spherical, and has a particular radius, typically 10.5 mm. This choice is advantageous from the fabrication point of view, but the anterior face of the crystalline lens when relaxed does not have a single spherical surface, but in reality an aspherical surface, with an infinite number of successive spherical surfaces.

Obviously an implant whose posterior spherical surface has only one radius is not able to espouse the anterior surface of the crystalline lens.

Similarly, the position relative to the anterior surface of the crystalline lens of precrystalline implants in which the posterior surface of the optic has a single radius of curvature is somewhat hit and miss. This results in some instability of the position of the implant relative to the crystalline lens.

Furthermore, most precrystalline implants are spaced apart from the anterior face of the crystalline lens and therefore avoid any contact with it.

WO-98/17205 describes an intraocular lens for a phakic eye adapted to be implanted between the anterior face of the crystalline lens and the iris, comprising an optical part formed on a central body and a haptic part, the posterior face of the lens having a central spherical first portion having a first radius and an annular spherical second surface portion having a second radius greater than the first radius. The radius of curvature of the central spherical first portion is much smaller than the radius of curvature of the anterior face of the crystalline lens, to reduce the probability of contact with the crystalline lens at the center. The diameter of the circumference of the haptic part is smaller than the diameter of the corresponding ciliary sulcus and the contact of the anterior face with the iris in order for the lens to be self-centering.

To this end, the present invention provides a precrystalline intraocular implant adapted to be implanted between the anterior face of the crystalline lens and the iris, the implant comprising an optical part formed on a central body without impeding accommodation and a haptic part.

According to a first aspect of the invention, the posterior face of the body includes a central spherical surface portion having a first radius, an annular spherical second surface portion having a second radius greater than the first radius, and a concentric spherical third surface portion surrounding the second portion and having a third radius greater than the second radius.

In a preferred embodiment of this aspect of the invention, the outside diameter of the peripheral ring is less than or equal to the diameter of the anterior face of the crystalline lens, and the peripheral ring therefore does not bear in the sulcus. In this case, a centered and stable position is ensured by the complementary shapes of the spherical surfaces of the posterior face of the body and the corresponding areas of the anterior face of the crystalline lens. In this embodiment, the haptic part of the concentric spherical third surface portion matches the corresponding part of the crystalline lens when relaxed. Large apertures in the haptic part protect the metabolism of the crystalline lens.

This preferred embodiment has an important advantage at the time of implantation. The implant must be released into the posterior chamber in front of the crystalline lens without worrying about placing the peripheral part in the ciliary sulcus, which the surgeon cannot see. Furthermore, because of the small thickness of this kind of implant and its small diameter, which is approximately 10 mm, the implant can be inserted through a 2 mm self-healing corneal or sclerotic-corneal incision. Finally, in this embodiment, the posterior surface of the implant espouses the interior face of the crystalline lens when relaxed in three areas with different radii, from the smallest at the center to the largest at the periphery.

According to another aspect of the invention, the peripheral ring of the haptic part is adapted to bear in the ciliary sulcus. The presence of this peripheral ring prohibits any decentering of the precrystalline intraocular implant in the posterior chamber. For this kind of implant, it is sufficient for the posterior face of the body to include a spherical central surface portion with a first radius and a spherical annular surface portion having a second radius greater than the first radius.

The haptic part preferably includes at least four radial arms of constant width and inclined toward the rear at an angle of 10°.

Thanks to the configuration of the posterior surface of the central body, the latter perfectly matches the convex shape of the surface of the anterior face of the crystalline lens, which minimizes the overall size and at the same time increases the actual surface area of contact between the posterior face of the central body and the crystalline lens.

With implants in accordance with either aspect of the invention, the radius of curvature of the anterior face of the central body, or each of the radii of curvature thereof, is calculated as a function of the ametropia to be corrected.

In one embodiment of the invention it is the whole of the body that constitutes the optical part, for example a monofocal optical part, and the anterior face of the body has a spherical central surface having a first radius and a spherical annular surface having a second radius. This kind of embodiment is particularly suitable for a convergent meniscus optic for correcting hypermetropia.

In another embodiment, it is only the central part of the body that defines the optical part, the body having a non-refractive ring around this central part. With this kind of body, the anterior surface can advantageously be spherical with a single radius of curvature in the case of a divergent optic for correcting myopia (i.e. concave or divergent meniscus optic).

Despite the resulting close contact between the posterior face of the central body of the implant and the anterior face of the crystal lens when relaxed, aqueous humor continues to circulate between these two surfaces, in particular because of anterior-posterior movements of the center of the crystalline lens on the occasion of accommodation, which modifies the radius of curvature of the central zone of the anterior face of the crystalline lens, and aqueous humor is aspirated into the space formed in this way between the body and the crystalline lens.

To enable the implant to be inserted through a small incision, the material of which the implant is made is flexible and highly hydrophilic and has a high refractive index. This kind of implant can have a minimum thickness close to 30 $\mu$m at the center of the optic for negative diopter implants for correcting myopias and 30 $\mu$m at the edge of the optic for positive diopter implants for correcting hypermetropias. For the contact with the iris and the crystalloid to have no physiological effect, the surface of the implant is made as smooth as possible, for example polished to a finish of 2 to 3 nm.

According to a preferred feature of the invention, the haptic part includes a peripheral ring and arms connecting the peripheral edge of the central body to the peripheral ring.

According to another preferred feature of the invention, the haptic part incorporates large diameter apertures delimited by a pair of arms, the edge of the body and the peripheral ring. These apertures in the haptic part of the intraocular implant, situated at the periphery of the crystalline lens, facilitate good contact of the aqueous humor with the anterior face of the equatorial region of the crystalline lens, despite the presence of the precrystalline intraocular implant on the anterior face of the crystalline lens.

This is because the metabolically active areas of the crystalline lens are on the anterior face of the crystalline lens, and more particularly at its equator, where cellular multiplication occurs and crystalline fibers are synthesized.

Other features and advantages of the invention will become more apparent in the course of the following description.

In the accompanying drawings, which are provided by way of nonlimiting example:

FIG. 1 is a front view of one embodiment of a precrystalline intraocular implant according to the invention;

FIG. 2 is a view in cross section of the precrystalline intraocular implant shown in FIG. 1;

FIG. 3 is a view in cross section of the precrystalline intraocular implant shown in FIG. 1, when in position in the posterior chamber of the eye;

FIG. 4 is a front view of a preferred embodiment of a precrystalline intraocular implant according to the invention;

FIG. 5 is a view in cross section of the precrystalline intraocular implant shown in FIG. 4;

FIG. 6 is a view in section of the precrystalline intraocular implant shown in FIG. 4, when in position in the posterior chamber of the eye;

FIG. 7 is a view in cross section of a different preferred embodiment of the precrystalline intraocular implant;

FIG. 8 is a view in section of the precrystalline intraocular implant shown in FIG. 7, when in position in the posterior chamber of the eye;

FIG. 9 is a view in cross section of a further preferred embodiment of the precrystalline intraocular implant;

FIG. 10 is a view in section of the precrystalline intraocular implant shown in FIG. 9, when in position in the posterior chamber of the eye; and FIG. 11 is a partial view in section and to a larger scale showing the radii of curvature of three concentric spherical portions of the posterior face of the implants shown in FIGS. 5, 7 and 9.

One embodiment of a precrystalline intraocular implant according to the invention is described first with reference to FIGS. 1 to 3.

The intraocular implant 10 is adapted to be positioned in the posterior chamber 4 of a phakic eye 1.

To be more precise, this intraocular implant 10 is implanted between the anterior face of the crystalline lens 2 and the iris 3.

The intraocular implant 10 has an optical part 6 for correcting an ametropia in an eye with a clear crystalline lens and a haptic part 7 adapted to support the optical part inside the eye.

In this nonlimiting example, the optical part 6 is adapted to correct myopia.

The intraocular implant 10 includes a central body 8 and a support structure 9 that globally surrounds the body.

The haptic part 7 includes a nonrefractive ring 12 on the central body 8 surrounding the optical area 11 that includes the optical part 6, a peripheral ring 14, and arms connecting the nonrefractive ring 12 to the peripheral ring 14.

In this example, the haptic part 7 has four radial arms, of constant width, spaced at 90° in quadrature around the nonrefractive ring 12.

Apertures 15 are therefore formed between the arms 13, the nonrefractive ring 12 and the peripheral ring 14.

The width of the radial arms 13 is preferably relatively small compared to the dimensions of the apertures 15.

The apertures 15 thus extend over a total angular sector much greater than 180°, allowing excellent contact of the aqueous humor with the anterior face of the crystalline lens 2 to which the intraocular implant 10 has just been fitted, and in particular its equatorial region.

Moreover, as can be seen better in FIG. 11, the arms 13 are connected to the nonrefractive ring 12 by thinned portions 16 which therefore form hinges at the junction of the arms 13.

Furthermore, blind holes 17 opening onto the anterior face are provided at the junction between the radial arms 13 and the peripheral ring 14, to facilitate manipulation of the implant when in place in the posterior chamber 4 of the eye.

As shown in FIG. 3, the intraocular implant conforming to this embodiment of the invention is adapted to position itself spontaneously on the anterior face of the relaxed crystalline lens 2, thanks to the complementary shapes of the posterior surface of the implant and the crystalline lens. Moreover, the peripheral ring 14 of the haptic part is adapted to bear in the ciliary sulcus 5 of the eye, which opposes decentering of the implant all around its circumference.

The posterior face 10A of the implant 10 includes at least two concentric spherical surface portions whose radii of curvature are substantially equal to the radii of curvature of the corresponding anterior face of the relaxed crystalline lens 2. As shown here, the posterior surface 10A of the body 8 includes a central surface portion 10B and an annular portion 10C and the central portion 10B has a radius of curvature (R1) less than the radius of curvature (R2) of the first annular portion 10C, and finally a second annular portion 10D surrounding the first annular portion 10C. In practice the radius of the central portion 10B is approximately 10.5 mm, or less, and the radius of the annular portion 10C is approximately 14 mm, or less.

To match the shape of the posterior chamber of the eye, the arms 13 are inclined toward the rear at an angle $\alpha$ substantially equal to 10° as far as the peripheral ring 14 of the haptic part of the implant 10.

The implant 10 therefore espouses as well as can be expected the shape of the posterior chamber of the eye, without modifying it, i.e. without rubbing on the iris 3 at the front or pushing on the crystalline lens 2 at the rear.

In practice, the optical area 11 of the body 8 of the implant can have a diameter equal to 4 mm in the case of correcting myopia. In the case of correcting hypermetropia, the optical area 11 has a diameter equal to that of the body 8 and the ring on the body is optical and not haptic.

The body 8 has a diameter substantially equal to 6 mm.

Finally, in order to bear in the ciliary sulcus, the peripheral ring 14 has an overall diameter substantially equal to 12 mm.

An embodiment conforming to another aspect of the invention is described next with reference to FIGS. 4 to 6, 7 and 8, 9 and 11. Unlike the embodiment shown in FIGS. 1 to 3, the peripheral ring 24 does not bear in the ciliary sulcus, but is held in position on the anterior face of the crystalline lens by the complementary shapes of the posterior surface of the implant and the anterior face of the crystalline lens, which it closely espouses (and possibly by contact with the posterior surface of the iris), in the manner of a contact lens between the cornea and the eyelid.

As shown in FIGS. 6, 8 and 10, an intraocular implant 20, 30, 40 can be implanted between the anterior face of the crystalline lens 2 and the iris 3 in a phakic eye 1. The implant has an optical part 6', a haptic part 7' and a central body 81 surrounded by a support structure 9'.

A central optical area 21 is formed on the central body 8' and can be identical to the central body 6 previously described, adapted to correct myopia, as shown in FIGS. 1 to 4.

Note that, because of the geometry of its anterior surface, this optical part is naturally adapted to correct any other ametropia of a phakic eye, and in particular hypermetropia, as shown in FIGS. 7 and 8.

In this case, the optical part 6' comprises a convergent meniscus lens of the kind routinely used to correct some kinds of hypermetropia.

The geometry of the anterior surface of the optical part can be adapted to correct myopia of the phakic eye, as shown in FIG. 9. This example corresponds to myopias from 0 to −12 diopters. In this case, the optical part 6' comprises a divergent meniscus lens. For stronger myopias (of more than −12 diopters in this example) the optic is biconcave, as shown in FIG. 5.

Generally speaking, the optical part of the implant can be adapted to correct presbyopia, in addition to the usual ametropias, by employing bifocal implant techniques, or even multifocal implant techniques, well known to the person skilled in the art, whilst retaining the spherical surface portions on the posterior face of the body.

As previously, the haptic part 7' of this intraocular implant 20, 40 includes a nonrefractive ring 22, 42 on the body 8' surrounding the optical area 21, a peripheral ring 24, 44, and arms 23, 43 connecting the nonrefractive ring 22, 42 of the body to the peripheral ring 24. On the other hand, in the intraocular implant 30, the haptic part 7' includes a peripheral ring 34 and arms 33 connecting the body to the peripheral ring 24.

To improve the circulation of the aqueous humor, the apertures 25 in the haptic part preferably extend over a total angular sector greater than or equal to 180°.

In this example, the haptic part includes radial arms 23, 33, 43 in the shape of angular sectors delimiting two by two apertures 25. One radial edge of one aperture can include a notch to identify the front face of the implant.

Here, each radial arm 23, 33, 43 and each aperture 25 extend over equal angular sectors.

Furthermore, to improve the flexibility of the implant, the haptic part also includes thinned portions 26, 36, 46 that form hinges at the junction of the arms 23, 33, 43 and the nonrefractive ring 22 on the central body 8'.

On the other hand, in contrast to the intraocular implant 10 conforming to the first embodiment shown in FIGS. 1 to 3, the overall dimensions of this intraocular implant 20, 30, 40 are significantly smaller, with the result that the peripheral ring 24 of the haptic part does not bear in the ciliary sulcus 5 of the eye, as shown in FIGS. 6, 8 and 10, and in practice does not extend beyond the periphery of the anterior face of the crystalline lens.

On the contrary, this precrystalline intraocular implant 20, 30, 40 is simply held between the anterior face of the crystalline lens and the iris, contact with which is inevitable, through a biconcave optical part (FIG. 6), or a convergent meniscus optical part (FIG. 8), or a divergent meniscus optical part (FIG. 10).

In order to remain centered in the posterior chamber 5, the precrystalline intraocular implant is adapted to adhere spontaneously to the anterior face of the relaxed crystalline lens 2 by virtue of the closely complementary shapes of the posterior surface and the anterior face of the crystalline lens.

To this end, the posterior face 20A, 30A, 40A of the implant 20, 30, 40 has three concentric surface portions 21A, 22A, 23A, 31A, 32A, 33A, 41A, 42A, 43A whose radii of curvature are substantially equal to the curvature of the corresponding anterior face of the relaxed crystalline lens 2.

As previously, the first two concentric surface portions 21A, 22A, 31A, 32A, 41A and 42A correspond to the central optical area 21, 31, 41 and to the ring 22, 32, 42 of the implant 20, 30, 40.

The third concentric surface portion 23A, 33A, 43A corresponds to the arms 23, 33, 43 and to the peripheral ring 24 of the haptic part of the intraocular implant 20, 30, 40.

This triple radius of curvature of the posterior face 20A, 30A, 40A of the implant 20, 30, 40 enables the implant to espouse closely the anterior face of the relaxed crystalline lens 2.

The presence of this third radius of curvature (R3) on the posterior face 20A, 30A, 40A of the implant 20, 30, 40 eliminates the need for a haptic peripheral ring bearing in the ciliary sulcus 5.

In a practical embodiment, described here by way of nonlimiting example, the central optical area 21, 31, 41 has a diameter substantially equal to 4 mm and the radius of curvature of its posterior face in the first portion 21A, 31A, 41A of the spherical surface is from 8 to 10.5 mm and preferably equal to 9.5 mm.

The ring 22, 32, 42 has a diameter substantially equal to 6 mm and the radius of curvature of its posterior face is from 12 to 14 mm and preferably substantially equal to 13 mm.

Finally, the radial arms 23, 33, 43, of which there are six in this example, and a peripheral ring 24 are inscribed in a circle having a diameter of at least 10 mm and preferably 11 mm. This dimension must be less than or equal to the diameter of the anterior face of the crystalline lens. The radius of curvature of the anterior and posterior faces of this portion of the implant, consisting of the radial arms 23, 33, 43 and the peripheral ring 24, is from 17 to 25 mm and preferably substantially equal to 17 mm.

As previously, note that the radii of curvature R1, R2, R3 of the posterior face of each of the implants 20, 30, 40 (FIG. 11) increases from the center toward the periphery of the implant, in order to obtain the best possible match to the topography of the posterior chamber defined by the anterior face of the crystalline lens 2, at the rear, and the posterior face of the iris, at the front.

In all three cases, this implant is accommodated as well as can be expected in the shape of the posterior chamber 4 without modifying it, i.e. without rubbing on the iris at the front or pushing on the crystalline lens at the rear, and achieves this with a minimum overall size.

It is also important to choose a sufficiently flexible material of maximum hydrophilia and with a high refractive index so that it can be inserted through a very short incision with minimum trauma.

It goes without saying that the material must also be stable in time, nonirritant and, of course, not cataractogenic.

For the presence of the implant to interfere with the crystalline lens as little as possible, it must have a minimum thickness close to 30 μm at the center in the case of an implant for correcting myopia and close to 30 μm at the edge of the body in the case of an implant for correcting hypermetropia.

It must also have the smoothest possible surface, for example a surface polished to a finish from 2 to 3 nm, to prevent long-term pigmentary dispersion through rubbing against the posterior face of the iris.

In particular, there being metabolically active areas only on the anterior face of the crystalline lens, where there are epithelial cells, and in particular at the equator of the crystalline lens, where cellular multiplication occurs and the crystalline fibers constituting the lens are synthesized, it is sufficient to protect the equator of the crystalline lens and to avoid trauma of the anterior face of the crystalline lens and the posterior face of the iris.

Furthermore, the energetic metabolism of the crystalline lens is diversified and in particular there is only moderate input of oxygen from the aqueous humor.

There is therefore no risk of the contact between the implant and the anterior face of the crystalline lens proving cataractogenic, especially given the extremely small thickness of the implant and its hydrophilic character.

Furthermore, despite the close contact obtained between the implant and the anterior face of the relaxed crystalline lens, circulation of aqueous humor between these two surfaces remains possible, because of anterior-posterior movements of the center of the crystalline lens during accommodation, which aspirates aqueous humor.

Thus the invention provides a precrystalline intraocular implant with optimum compatibility for the anatomy and the physiology of the posterior chamber of the eye.

Of course, the embodiments described can be modified in numerous ways without departing from the scope of the invention. In particular, the precrystalline intraocular implant according to the invention can be a multifocal implant for correcting presbyopia. In this case, the anterior face of the implant can include, for example, in accordance with a technique known in the art, a central optical area and a plurality of concentric annular optical areas, with appropriate radii of curvature.

The width of the arms of the haptic part could differ from one arm to another, rather than being constant. The same applies to the haptic part in general.

What is claimed is:

1. A precrystalline intraocular implant adapted to be implanted between an anterior face of the crystalline lens (2) and the iris, the implant comprising an optical part (6') formed on a central body (8') of an optical implant and a haptic part (7'), a posterior face of the body including a central spherical first portion (21A, 31A, 41A) having a first radius (R1), an annular spherical second surface portion (22A, 32A, 42A) having a second radius (R2) greater than the first radius, characterized in that a concentric spherical third portion surrounds the second portion and has a third radius (R3) greater than the second radius (R2).

2. A precrystalline intraocular implant according to claim 1, characterized in that the radii of curvature (R1, R2, R3) of said surface portions correspond to those of the anterior face of the crystalline lens (2) when relaxed.

3. A precrystalline intraocular implant according to claim 1, characterized in that the whole of the body (8') constitutes a monofocal optical part (6') and the anterior face of the body includes a spherical central surface having a first radius and an annular surface having a second radius.

4. A precrystalline intraocular implant according to claim 1, characterized in that the optical part (6') comprises only a central area (21, 41) of the body, which has a haptic ring (22, 42) surrounding the optical part.

5. A precrystalline intraocular implant according to claim 1, characterized in that the haptic part (7') includes a peripheral ring (24) and arms (23, 33, 43) connecting the peripheral edge of the body (8') and the peripheral ring (24).

6. A precrystalline intraocular implant according to claim 5, characterized in that the haptic part (7') includes large apertures (25) delimited by a pair of arms (23, 33, 43), the peripheral edge of the body (8'), and the peripheral ring (24).

7. A precrystalline intraocular implant according to claim 5, characterized in that the haptic part (7') includes apertures (25) extending over a total angular sector greater than or equal to 180°.

8. A precrystalline intraocular implant according to claim 5, characterized in that the haptic part (7') includes at least four radial arms (23, 33, 43) of the same width.

9. A precrystalline intraocular implant according to claim 5, characterized in that the haptic part (7') includes radial arms (23, 33, 43) in the form of angular sectors delimiting apertures (35).

10. A precrystalline intraocular implant according to claim 1, characterized in that the posterior face of the implant (21A, 31A, 41A) is conformed to adhere spontaneously to the anterior face of the relaxed crystalline lens.

11. A precrystalline intraocular implant according to claim 10, characterized in that the concentric spherical third surface portion corresponding to the arms (23, 33, 43) and to the peripheral ring (24) has a radius of curvature (R3) substantially equal to the radius of curvature in the equatorial region of the anterior face of the relaxed crystalline lens (2) and the diameter of the peripheral ring (24) is adapted to match the diameter of the crystalline lens.

12. A precrystalline intraocular implant adapted to be implanted between an anterior face of the crystalline lens (2) and the iris, comprising; an optical part (6) formed on a central body (8) and a haptic part (7), a posterior face of the body including a central spherical portion (10B) having a first radius (R1) and a spherical annular surface portion (10C) having, a second radius (R2) greater than the first radius, characterized in that a periphery of the haptic part is conformed to bear in the ciliary sulcus (5).

13. A precrystalline intraocular implant according to claim 12, characterized in that the radii of curvature (R1, R2) of said surface portions correspond to those of the anterior face of the relaxed crystalline lens 2.

14. A precrystalline intraocular implant according to claim 12, characterized in that the optical part (6) comprises only a central area (11) of the body, the body having a haptic ring (12) surrounding the optical part.

15. A precrystalline intraocular implant according to claim 12, characterized in that the haptic part (7) includes a peripheral ring (14) and arms (13) connecting the peripheral edge of the body (8') and the peripheral ring (14).

16. A precrystalline intraocular implant according to claim 15, characterized in that the haptic part (7) includes large apertures (15) delimited by a pair of arms (13), the peripheral edge of the body (8), and the peripheral ring (14).

17. A precrystalline intraocular implant according to claim 15, characterized in that the haptic part (7) includes apertures (15) extending over a total angular sector greater than or equal to 180°.

18. A precrystalline intraocular implant according to claim 15, characterized in that the haptic part (7) includes at least four radial arms 13) of the same width.

19. A precrystalline intraocular implant according to claim 15, characterized in that the haptic part (7) includes radial arms (13) in the form of angular sectors delimiting apertures (25).

20. A precrystalline intraocular implant according to claim 12, characterized in that the posterior face of the implant (10A) is conformed to adhere spontaneously to the anterior face of the crystalline lens.

21. A precrystalline intraocular implant according to claim 15, characterized in that said arms (13) are inclined to the rear at an angle of substantially 10° as far as the peripheral ring (14).

* * * * *

UNITED STATES PATENT AND TRADEMARK OFFICE
CERTIFICATE OF CORRECTION

PATENT NO. : 6,749,633 B1
DATED : June 15, 2004
INVENTOR(S) : George Lorenzo et al.

It is certified that error appears in the above-identified patent and that said Letters Patent is hereby corrected as shown below:

Title page,
After Item [87], please insert Item [30] as follows:
-- [30]  Foreign Application Priority Data
   Nov. 10, 1999   (FR)................9914156 --.

Signed and Sealed this

Nineteenth Day of October, 2004

JON W. DUDAS
*Director of the United States Patent and Trademark Office*